(12) United States Patent
Park (10) Patent No.: US 10,301,354 B2
(45) Date of Patent: May 28, 2019

(54) ANTIBACTERIAL AND FUNGICIDAL PEPTIDE IN WHICH LYSINE AND TRYPTOPHAN RESIDUES ARE REPEATED, AND USE THEREOF

(71) Applicant: Industry-Academic Cooperation Foundation, Chosun University, Gwangju (KR)

(72) Inventor: Yoon Kyung Park, Jeollanam-do (KR)

(73) Assignee: Industry-Academic Cooperation Foundation, Chosun University, Gwangju (KR)

(*) Notice: Subject to any disclaimer, the term of this patent is extended or adjusted under 35 U.S.C. 154(b) by 0 days.

(21) Appl. No.: 15/833,875

(22) Filed: Dec. 6, 2017

(65) Prior Publication Data

US 2018/0179251 A1 Jun. 28, 2018

Related U.S. Application Data

(60) Division of application No. 14/318,106, filed on Jun. 27, 2014, now abandoned, which is a continuation-in-part of application No. PCT/KR2012/011781, filed on Dec. 28, 2012.

(30) Foreign Application Priority Data

Dec. 30, 2011 (KR) .................. 10-2011-0147577

(51) Int. Cl.
| | |
|---|---|
| C07K 5/103 | (2006.01) |
| C07K 7/06 | (2006.01) |
| C07K 5/11 | (2006.01) |
| C07K 7/08 | (2006.01) |
| A61K 38/00 | (2006.01) |

(52) U.S. Cl.
CPC ............ *C07K 5/101* (2013.01); *C07K 5/1019* (2013.01); *C07K 7/06* (2013.01); *C07K 7/08* (2013.01); *A61K 38/00* (2013.01); *Y02A 50/473* (2018.01); *Y02A 50/481* (2018.01)

(58) Field of Classification Search
CPC ...... A61K 38/00; C07K 5/101; C07K 5/1019; C07K 7/06; C07K 7/08
See application file for complete search history.

(56) References Cited

U.S. PATENT DOCUMENTS

| | | | |
|---|---|---|---|
| 6,743,769 B1 | 6/2004 | Yeaman et al. | |
| 7,902,327 B2 | 3/2011 | Kallenbach et al. | |
| 2007/0244044 A1* | 10/2007 | O'Neil ................. | C07K 5/0817 514/1.8 |
| 2008/0032934 A1 | 2/2008 | Ellis-Behnke et al. | |

OTHER PUBLICATIONS

"N-Terminal Acetylation and C-Terminal Amidation of Peptides," Thermo Scientific Technical Information, pp. 1-2, 2004.
Dathe et al. "Peptide Helicity and Membrane Surface Charge Modulate the Balance of Electrostatic and Hydrophobic Interactions with Lipid Bilayers and Biological Membranes," *Biochemistry*, 35(38):12612-12622 (1996).
Epand et al., "Direct Comparison of Membrane Interactions of Model Peptides Composed of Only Leu and Lys Residues," *Biopolymers* 71:2-16, 2003.
Gopal et al. "Effect of Leucine and Lysine substitution on the antimicrobial activity and evaluation of the mechanism of the HPA3NT3 analog peptide," *J. Pept. Sci.*, 15:589-594 (2009).
Gopal et al. "Reversed sequence enhances antimicrobial activity of synthetic peptide," *J. Pept. Sci.*, 17:329-334 (2011).
Gopal et al., "Antifungal Activity of $(KW)_n$ or $(RW)_n$ Peptide Against *Fusarium solani* and *Fusarium oxysporum*," *Int J Mol Sci.* 13:15042-15053, 2012.
Gopal et al., "Effect of Repetitive Lysine-Tryptophan Motifs on the Bactericidal Activity of Antimicrobial Peptides," *Amino Acids* 44:645-660, 2013.
Liu, "Length Effects in Antimicrobial Peptides of the (RW)n Series," *Antimicrobial Agents and Chemotherapy*, p. 597-603, Feb. 2007.
Park et al., "A Leu-Lys-Rich Antimicrobial Peptide: Activity and Mechanism," *Biochim Biophys Acta.* 1645:172-182, 2003.
Rosenfeld et al., "Effect of the Hydrophobicity to Net Positive Charge Ratio on Antibacterial and Anti-Endotoxin Activities of Structurally Similar Antimicrobial Peptides," *Biochemistry* 49:853-861, 2010.
Song et al. "Cell Selectivity and Mechanism of Action of Antimicrobial Model Peptides Containing Peptoid Residues," *Biochemistry*, 44(36):12094-12106 (2005).
UniProt Protein Database, Protein Accession C5JGW0, Extracellular lipase, accessed on Jun. 12, 2004.
UniProt Protein Database, Protein Accession F6GSD1, Glucosyltransferase 1c, accessed on Oct. 16, 2015.
Wang et al., "Cell Selectivity and Anti-Inflammatory Activity of a Leu/Lys-Rich α-Helical Model Antimicrobial Peptide and Its Diastereomeric Peptides," *Peptides* 31:1251-1261, 2010.
Zhong, "Synthesis, Characterization, and Thermodynamic Study of a Polyvalent Lytic Peptide-Polymer Conjugate As Novel Anticancer Agent," *Bioconjugate Chem.*, 21, 2055-2064, 2010.

* cited by examiner

*Primary Examiner* — Rachael E Bredefeld
*Assistant Examiner* — Erinne R Dabkowski
(74) *Attorney, Agent, or Firm* — Klarquist Sparkman, LLP (57) ABSTRACT

The present invention relates to an antibacterial and fungicidal peptide in which a lysine and tryptophan dipeptide is repeated. More specifically, the antibacterial and fungicidal peptide of the present invention, in which lysine and tryptophan dipeptide is repeated four times, shows excellent antibacterial activities with respect to gram-positive bacteria, gram-negative bacteria and antibiotic-resistant strains by affecting the inner membrane of harmful microorganisms, has remarkable fungicidal activities with respect to pathogenic fungi and antibiotic-resistant fungi, and shows little cytotoxicity, and thus can be useful for a pharmaceutical composition, a cosmetic composition, agricultural chemicals, a food preservative, a cosmetic preservative, and a pharmaceutical preservative.

18 Claims, 7 Drawing Sheets

Specification includes a Sequence Listing.

FIG.1

| Peptide | Amino acid sequence |
|---|---|
| SEQ. ID. NO: 1: $(KW)_2$ | KWKW-$NH_2$ |
| SEQ. ID. NO: 2: $(KW)_3$ | KWKWKW-$NH_2$ |
| SEQ. ID. NO: 3: $(KW)_4$ | KWKWKWKW-$NH_2$ |
| SEQ. ID. NO: 4: $(KW)_5$ | KWKWKWKWKW-$NH_2$ |

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Amino acid sequence for (KW)2

<400> SEQUENCE: 1

Lys Trp Lys Trp
1

<210> SEQ ID NO 2
<211> LENGTH: 6
<212> TYPE: PRT
<213> ORGANISM: Artificial Sequence
<220> FEATURE:
<223> OTHER INFORMATION: Amino acid sequence for (KW)3

<400> SEQUENCE: 2

Lys Trp Lys Trp Lys Trp
1               5

<210> SEQ ID NO 3
<211> LENGTH: 8
<212> TYPE: PRT
<213> ORGANISM: Artificial Sequence
<220> FEATURE:
<223> OTHER INFORMATION: Amino acid sequence for (KW)4

<400> SEQUENCE: 3

Lys Trp Lys Trp Lys Trp Lys Trp
1               5

<210> SEQ ID NO 4
<211> LENGTH: 10
<212> TYPE: PRT
<213> ORGANISM: Artificial Sequence
<220> FEATURE:
<223> OTHER INFORMATION: Amino acid sequence for (KW)5

<400> SEQUENCE: 4

Lys Trp Lys Trp Lys Trp Lys Trp Lys Trp
1               5                   10
```

ANTIBACTERIAL AND FUNGICIDAL PEPTIDE IN WHICH LYSINE AND TRYPTOPHAN RESIDUES ARE REPEATED, AND USE THEREOF

CROSS REFERENCE TO RELATED APPLICATIONS

This application is a divisional of U.S. patent application Ser. No. 14/318,106, filed Jun. 27, 2014, which is a Continuation-In-Part of PCT Patent Application No. PCT/KR2012/011781, filed Dec. 28, 2012, which claims priority to Korean Patent Application No. KR 10-2011-0147577, filed Dec. 30, 2011.

BACKGROUND OF THE INVENTION

1. Field of the Invention

The present invention relates to a novel antibiotic peptide in which lysine and tryptophan residues are repeated and an antibacterial and fungicidal pharmaceutical composition comprising the same as an active ingredient.

2. Description of the Related Art

The bacterial infection is one of the most common and lethal causes of human disease. Unfortunately, misuse or overuse of antibiotics brought antibiotic resistance of bacteria. In fact, the period that it takes for bacteria to show resistance against a new antibiotic is much shorter than the period for the development of a novel antibiotic or analogues thereof. For example, fatal bacteria *Enterococcus faecalis, Mycobacterium tuberculosis* and *Pseudomonas aeruginosa* have raised their resistance against almost every antibiotics developed so far (Stuart B. Levy, *Scientific American*, 46-53, 1998).

Tolerance against antibiotics is different from resistance against antibiotics. Antibiotic tolerance was first observed in *Pneumococcus* sp. in 1970s with providing an important clue to understand the mechanism of the action of penicillin (Tomasz et al., *Nature*, 227, 138-140, 1970). Such species of bacteria that show tolerance stop growing in the presence of a common concentration of antibiotics but cannot be killed. Tolerance is developed when autolytic enzyme such as autolysin is not activated in the presence of an antibiotic that inhibits cell wall synthase. Penicillin kills bacteria by activating endogenous hydrolytic enzyme, but the bacteria, on the contrary, inhibit the enzyme activity to survive in the presence of antibiotics.

It is a clinically very important phenomenon that bacteria have tolerance against antibiotics. That is, once it is impossible to kill the bacteria having tolerance, the treatment effect of antibiotics on infectious disease decreases (Handwerger and Tomasz, *Rev. Infec. Dis.*, 7, 368-386, 1985). Tolerance is regarded as a precondition for the coming resistance against antibiotics in bacteria. That means even after the treatment with antibiotics, some strains still survive. These strains acquire a new genetic element to build resistance against antibiotics, so that they can continue to survive in the presence of antibiotics. All the strains showing resistance against antibiotics also have tolerance against those antibiotics as well (Liu and Tomasz, *J. Infect. Dis.*, 152, 365-372, 1985). Therefore, it is urgent request to develop a novel antibiotic that is able to kill the strain having antibiotic resistance.

Tolerance is largely divided into two groups according to its mechanism. First, phenotypic tolerance is the one that is observed when the growth rate decreases in every strain (Tuomanen E., *Revs. Infect. Dis.*, 3, S279-S291, 1986). The other one is genetic tolerance developed by mutation in some specific strains. The basic and common phenomenon in both cases is the down regulation of autolytic enzyme activity. This down regulation is temporary when it is phenotypic tolerance caused by an external stimulus, but is permanent when it is genetic tolerance caused by mutation in regulatory pathways controlling cell hemolysis. Precisely, the most simple genetic tolerance is caused by the deletion of autolytic enzyme. It is very rare for a strain to have tolerance with the deletion of autolytic enzyme caused by some unknown reasons. However, tolerance observed clinically in strains is mostly caused by the phenotypic regulation of autolytic enzyme activity (Tuomanen et al., *J. infect. Dis.*, 158, 36-43, 1988).

As explained hereinbefore, it is required to develop a novel antibiotic to eliminate antibiotic-resistant bacteria which is functioning independently from autolytic enzyme activity.

In the meantime, bacteria can kill other neighboring bacteria by synthesizing peptides or small organic molecules, called 'bacteriocin'. The bacteriocin is divided into three groups according to the structural characteristics; which are lantibiotics, nonlantibiotics, and those secreted by signal peptides (Cintas et al., *J. Bad.*, 180, 1988-1994, 1998). Animals including insects can self-produce such peptide antibiotics (Bevins et al., *Ann. Rev. Biochem.*, 59, 395-414, 1990), which are also divided into three groups according to the structure. First group is cysteine-rich β-sheet peptide, the second group is α-helical amphiphilic peptide, and the third group is proline-rich peptide (Mayasaki et al., *Int. J. Antimicrob. Agents*, 9, 269-280, 1998). Such antibacterial peptides are known to play an important role in host defense and innate immune system (Boman, H. G., *Cell*, 65:205, 1991; Boman, H. G., *Annu. Rev. Microbiol.*, 13:61, 1995). The said antibacterial peptides have different structures determined by the amino acid sequences, among which the most common structure is α-helical amphiphilic form without cysteine residues, as shown in cecropin, the antibacterial peptide found in insects.

The antibacterial activity of amphiphilic peptide has been well studied, based on which the attempts have been made to develop antibiotics. Melittin is the peptide taking at least 50% of solid components of bee venom, in which C-terminal is amidated and cytotoxicity against eukaryotic cell is strong enough to destroy mammalian cells even at a low concentration and antibacterial activity against such microorganisms as Gram-negative bacteria and Gram-positive bacteria is excellent (Habermann, E., *Science*, 177: 314, 1972; Steiner, H., et al., *Nature*, 292: 246, 1981; Tosteson, M. T., et al., *Biochemistry*, 228: 337, 1987). Cecropin amphiphilic peptide having HP(2-20) like amino acid sequence was first found in fruit fly and found later on in silkworm pupa and in small intestine of pig. Particularly, according to the previous reports, cecropin A (CA) exhibits high antibacterial activity but has only minor antifungal and anticancer activity (Boman, H. G. and Hultmark, D., *Annu. Rev. Microbiol.*, 41: 103, 1987).

In addition to the studies on the activity of the mentioned amphiphilic peptide, the amino acid sequence and protein structure have also been studied, saying that the characteristics of the sequence are closely related to the antibacterial activity. For example, when arginine is substituted with lysine therein, the activity still remains but cytotoxicity against eukaryotic cell is reduced (Epand R F, Lehrer R I, Waring A, Wang W, Maget-Dana R, Lelievre D, Epand R M., *Bioploymers* 2003; 71: 2-16.; Park Y, Lee D G, Jang S H, Woo E R, Jeong H G, Choi C H, Hahm K S., *Biochim. Biophys. Acta* 2003; 1645: 172-182.). A strong synthetic antibacterial peptide composed of lysine residues alone is located on the polar surface of amphiphilic structure and interacts with the upper section of anionic lipid, which gives the specificity to microorganism (DatheM, SchumannM, WieprechtT, WinklerA, BeyermannM, Krause E, Matsuzaki K, Murase O, Bienert M., *Biochemistry* 1996; 35: 12612-12622.; Song Y M, Park Y, Lim S S, Yang S T, Woo E R, Park I S, Lee J S, Kim J I, Hahm K S, Kim Y, Shin S Y., *Biochemistry* 2005; 44: 12094-12106.; Gopal R, Park S C, Ha K J, Cho S J, Kim S W, Song P I, Nah J W, Park Y, Hahm K S., *J. Pept. Sci.* 2009; 15: 589-594.).

Therefore, the present inventors synthesized peptides in various lengths, in which lysine and tryptophan residues form KW dipeptides that are repeated 2-5 times. The present inventors eventually completed this invention by confirming that the peptides of the invention, particularly $(KW)_4$ represented by SEQ. ID. NO: 3 had excellent antibacterial activity against Gram-positive, Gram-negative, and antibiotic-tolerant strains and excellent fungicidal activity against pathogenic fungi and antibiotic-tolerant fungi by affecting the inner membrane of the pathogenic microorganism but has least cytotoxicity, suggesting that the peptides of the present invention can be functioning as safe antibacterial and fungicidal drugs to humans.

The present inventors also investigated the antibacterial activity of $(KW)_3$ in which lysine and tryptophan residues are repeated three times (Gopal R, Kim Y J, Seo C H, Hahm K S, Park Y., J Pept Sci. 2011; 17: 329-334). As a result, it was confirmed that $(KW)_4$ of the invention demonstrated 16 times higher antibacterial activity in general strains and 8 times higher antibacterial activity in antibiotic-tolerant strains than $(KW)_3$, along with excellent antifungal activity. In conclusion, $(KW)_4$ was confirmed to be a better peptide in its antibacterial and antifungal activity than $(KW)_3$.

SUMMARY OF THE INVENTION

It is an object of the present invention to provide an antibacterial and fungicidal peptide in which lysine and tryptophan residues are repeated.

It is another object of the present invention to provide an antibacterial and fungicidal composition comprising the said antibacterial and fungicidal peptide.

To achieve the above objects, the present invention provides an antibacterial or fungicidal peptide in which lysine and tryptophan are repeated.

The present invention also provides an antibacterial or fungicidal pharmaceutical composition comprising the said peptide as an active ingredient.

The present invention also provides an antibacterial or fungicidal cosmetic composition comprising the said peptide as an active ingredient.

The present invention also provides a non-toxic agricultural pesticide comprising the said peptide as an active ingredient.

The present invention also provides a preservative for medicine, cosmetics, food, or feed comprising the said peptide as an active ingredient.

The present invention also provides a method for suppressing bacteria or fungi containing the step of treating a pharmaceutically effective dose of the said antibacterial or fungicidal pharmaceutical composition to the target bacteria or fungi to suppress them.

The present invention also provides a method for treating the pathogenic bacteria or fungi caused disease containing the step of administering a pharmaceutically effective dose of the said antibacterial or fungicidal pharmaceutical composition to a subject having the pathogenic bacteria or fungi caused disease.

The present invention also provides a method for preventing the pathogenic bacteria or fungi caused disease containing the step of administering a pharmaceutically effective dose of the said antibacterial or fungicidal pharmaceutical composition to a subject.

The present invention also provides a use of the said peptide for the preparation of an antibacterial or fungicidal pharmaceutical composition.

The present invention also provides a use of the said peptide for the preparation of an antibacterial or fungicidal cosmetic composition.

The present invention also provides a use of the said peptide for the preparation of a non-toxic agricultural pesticide.

The present invention also provides a use of the said peptide for the preparation of a preservative for medicine, cosmetics, food, or feed.

The present invention also provides the peptide usable for the suppression of pathogenic bacteria or fungi.

In addition, the present invention provides the peptide usable for treating or preventing the pathogenic bacteria or fungi caused disease.

Advantageous Effect

As explained hereinbefore, the antibacterial and fungicidal peptide of the present invention in which lysine and tryptophan residues are repeated demonstrates excellent antibacterial activity against Gram-positive, Gram-negative, and antibiotic-tolerant strains and excellent fungicidal activity against pathogenic fungi and antibiotic-tolerant fungi by affecting the inner membrane of the pathogenic microorganism but has least cytotoxicity, so that it can be effectively used as a pharmaceutical composition, a cosmetic composition, an agricultural pesticide, a food preservative, a cosmetic preservative, and a medicine preservative.

BRIEF DESCRIPTION OF THE DRAWINGS

The application of the preferred embodiments of the present invention is best understood with reference to the accompanying drawings, wherein:

FIG. 2A: maximum fluorescent light emission wavelength values of $(KW)_4$ and $(KW)_5$ in water FIG. 2B maximum fluorescent light emission wavelength values of $(KW)_4$ and $(KW)_5$ in PBS $(KW)_4$(●), $(KW)_5$(▲)

FIG. 2C: $(KW)_4$ structure in PBS

FIG. 2D: $(KW)_5$ structure in PBS

25 μM(●), 50 μM(■), 100 μM(▲), 150 μM(◆)

FIG. 3A: antibiotic-tolerant *E. coli* (*E. coli* CCARM 1229)

FIG. 3B: antibiotic-tolerant *Staphylococcus aureus* (*S. aureus* CCARM 3090)

FIG. 4A: membrane depolarization of antibiotic-tolerant *E. coli* (*E. coli* CCARM 1229)

FIG. 4B: membrane depolarization of antibiotic-tolerant *Staphylococcus aureus* (*S. aureus* CCARM 3090)

FIG. 4C: effect on inner membrane of *E. coli*

FIG. 4D: effect on inner membrane of *Staphylococcus aureus* (*S. aureus*)

FIG. 4E antibacterial activity against antibiotic-tolerant *E. coli* (*E. coli* CCARM 1229)

FIG. 4F: antibacterial activity against antibiotic-tolerant *Staphylococcus aureus* (*S. aureus* CCARM 3090)

FIGS. 4A-4D: $(KW)_2(♦)$, $(KW)_3(■)$, $(KW)_4(●)$, $(KW)_5(▲)$, Melittin(○)

FIGS. 4E-4F: $(KW)_4$ MIC(□), $(KW)_4$ 2MIC(Δ), $(KW)_5$ MIC(■), $(KW)_5$ 2MIC(▲)

FIG. 5A: PE:PG(7:3, w/w)

FIG. 5B: PC:CH(10:1, w/w)

FIG. 5C: PE:PG(7:3, w/w)

$(KW)_2(♦)$, $(KW)_3(■)$, $(KW)_4(●)$, $(KW)_5(▲)$

FIG. 6A: PE:PG(7:3, w/w)

FIG. 6B: PC:CH(10:1, w/w)

$(KW)_2(♦)$, $(KW)_3(■)$, $(KW)_4(●)$, $(KW)_5(▲)$

FIG. 7A: negative control (non-treated)

FIG. 7B: $(KW)_4$

DESCRIPTION OF THE PREFERRED EMBODIMENTS

Hereinafter, the present invention is described in detail.

The present invention provides an antibacterial and fungicidal peptide in which the lysine and tryptophan (KW) dipeptide is repeated.

The lysine and tryptophan KW dipeptide is preferably repeated 1-10 times, and more preferably 4 times, or at least 4 times, but not always limited thereto. In particular embodiments the KW dipeptide is repeated 4-10 times, or 4-5 times.

The said peptide is composed of the amino acid sequence represented by SEQ. ID. NO: 3; hardly has cytotoxicity; is easy to be synthesized because of its short length comprising the minimum 8-mer amino acids; and has amphiphilicity owing to the enlarged hydrophobic region, but not always limited thereto.

The said peptide has the antibacterial activity preferably against Gram-positive bacteria, Gram-negative bacteria, and antibiotic-tolerant strains, and more precisely the Gram-positive bacteria are selected from the group consisting of *Bacillus subtilis, Staphylococcus aureus* and *Listeria monocytogenes*, and the Gram-negative bacteria are selected from the group consisting of *Escherichia coli, Psedomonas aeruginosa* and *Salmonella typhimurium*. In the meantime, the antibiotic-tolerant strains are preferably selected from the group consisting of *E. coli* (*E. coli* CCARM 1229, 1238), *Salmonella* (*S. typhimurium* CCARM 8007, 8009, 8013) and *Staphylococcus* (*S. aureus* CCARM 3089, 3090, 3108, 3114, 3126), but not always limited thereto.

The said peptide has the fungicidal activity preferably against pathogenic fungi and antibiotic-tolerant fungi, and more precisely the said pathogenic fungi are selected from the group consisting of *Candida albicans, C. catenulate, C. intermidia, C. rugosa, C. glabrata* and *C. melibiosica*, and the antibiotic-tolerant fungi are preferably *C. albicans* CCARM 14001, 14007, and 14020, but not always limited thereto.

In addition, the said peptide is conjugated to the outer wall of antibiotic-tolerant *E. coli* (*E. coli* CCARM 1229) and antibiotic-tolerant *Staphylococcus aureus* (*S. aureus* CCARM 3090) in order to be functioning there and further invades into the inner wall to affect them. Thus, when the peptide is treated to antibiotic-tolerant *E. coli* (*E. coli* CCARM 1229), it makes the surface of the strain rough and injured to cause aggregation there, but the function is not always limited thereto.

To prepare a novel antibacterial and fungicidal peptide, the present inventors synthesized the peptide which is short and has a simple sequence composed of only two kinds of amino acids, lysine and tryptophan. As a result, the inventors synthesized $(KW)_2$ (SEQ. ID. NO: 1) in which lysine and tryptophan residues are repeated twice, $(KW)_3$ (SEQ. ID. NO: 2) in which those residues are repeated three times, $(KW)_4$ (SEQ. ID. NO: 3) in which those residues are repeated four times, and $(KW)_5$ (SEQ. ID. NO: 4) in which those residues are repeated 5 times (see FIG. 1).

To investigate the antibacterial activity of the peptide of the present invention, the present inventors used $(KW)_n$ (n=2, 3, or 5) peptides in different lengths and Melittin peptide as controls. Minimal inhibitory concentration (referred as "MIC" hereinafter) that was the concentration each strain could survive without being divided was measured from all the groups. At this time, Gram-positive bacteria used for the investigation were *Bacillus subtilis, Staphylococcus aureus* and *Listeria monocytogenes*, and Gram-negative bacteria used for the measurement were *Escherichia coli, Psedomonas aeruginosa* and *Salmonella typhimurium*. Also, the antibiotic-tolerant strains used herein were *E. coli* (*E. coli* CCARM 1229, 1238), *Salmonella* (*S. typhimurium* CCARM 8007, 8009, 8013) and *Staphylococcus* (*S. aureus* CCARM 3089, 3090, 3108, 3114, 3126). As a result, the peptide of the present invention represented by SEQ. ID. NO: 3 demonstrated antibacterial activity in the general strains 64 times higher than the control peptide represented by SEQ. ID. NO: 1, 16 times higher than the peptide represented by SEQ. ID. NO: 2, and 8 times higher than the peptide represented by SEQ. ID. NO: 4. In the meantime in the antibiotic-tolerant strains, the peptide of the present invention showed the antibacterial activity 32 times, times, and 8 times higher than the above peptides, respectively (see Table 1). Therefore, the peptide of the present invention was confirmed to have excellent antibacterial activity against all the Gran-positive bacteria, Gram-negative bacteria, and antibiotic-tolerant strains.

To investigate the fungicidal activity of the peptide of the present invention, MIC was measured by using pathogenic fungi such as *Candida albicans, C. catenulate, C. intermidia, C. rugosa, C. glabrata* and *C. melibiosica* and antibiotic-tolerant fungi such as *C. albicans* CCARM 14001, 14007 and 14020. As a result, the peptide of the present invention represented by SEQ. ID. NO: 3 demonstrated excellent fungicidal activity regardless of solution used for the experiment and the peptide represented by SEQ. ID. NO: 4 showed excellent fungicidal activity in PBS (see Table 2). The peptides each represented by SEQ. ID. NO: 3 and NO: 4 were confirmed to have excellent fungicidal activity against antibiotic-tolerant fungi (see Table 3).

The present inventors also investigated cytotoxicity of the peptide of the invention. To do so, hemolytic activity of the peptide was measured. As a result, the peptide represented by SEQ. ID. NO: 3 hardly showed cytotoxicity (see Table 4).

The present inventors also investigated aggregation and the structure of the peptide by using a spectrofluorometer and circular dichroism (CD). As a result, the peptide represented by SEQ. ID. NO: 3 did not show aggregation in water nor in PBS, but the peptide represented by SEQ. ID. NO: 4 showed aggregation in PBS (see FIGS. 2A-2D).

To investigate the acting site of the peptide of the present invention in *E. coli*, confocal laser scanning microscopy was used. As a result, it was observed that the peptide represented by SEQ. ID. NO: was conjugated to the outer wall of antibiotic-tolerant *E. coli* (*E. coli* CCARM 1229) and antibiotic-tolerant *Staphylococcus aureus* (*S. aureus* CCARM 3090) (see FIGS. 3A-3B).

The present inventors also investigated whether or not the peptide of the invention could actually affect the membrane of *E. coli* and how fast the peptide could kill the bacteria by performing depolarization analysis, observation of action on inner cell membrane, and measurement of apoptosis over the time. As a result, the peptide represented by SEQ. ID. NO: 1 could not induce depolarization in antibiotic-tolerant *E. coli* (*E. coli* CCARM 1229) nor in antibiotic-tolerant *Staphylococcus aureus* (*S. aureus* CCARM 3090). The peptide represented by SEQ. ID. NO: 2 induced depolarization approximately 20% at the concentration of 50 µM, while the peptides represented by SEQ. ID. NO: 3 and SEQ. ID. NO: 4 induced depolarization approximately 80% at the concentration of 25 µM in both strains (see FIGS. 4A and 4B). The peptides represented by SEQ. ID. NO: 3 and SEQ. ID. NO: 4 were able to affect inner membrane of *E. coli* and *Staphylococcus aureus* (see FIGS. 4C and 4D). The peptide represented by SEQ. ID. NO: 3 showed faster antibacterial activity against antibiotic-tolerant *E. coli* (*E. coli* CCARM 1229) and antibiotic-tolerant *Staphylococcus aureus* (*S. aureus* CCARM 3090) than the peptide represented by SEQ. ID. NO: 4 did.

The present inventors also investigated whether or not the peptide of the invention could take direct action on bacteria and erythrocyte-like liposome and whether or not the peptide could coagulate bacteria-like liposome by using a spectrofluorometer. As a result, both the peptide represented by SEQ. ID. NO: and the peptide represented by SEQ. ID. NO: 4 took action against bacteria-like liposome in the presence of L-a-phosphatidylethanolamine (PE) and L-a-phosphatidylglycerol (PG) (7:3). However, in the presence of egg yolk L-a-phosphatidylcholine (PC) and cholesterol (CH) at the ratio of 10:1, the peptide represented by SEQ. ID. NO: 3 emitted the fluorescence less than half the amount emitted by the peptide represented by SEQ. ID. NO: 4 at the same concentration (see FIGS. 5A and 5B). The peptide represented by SEQ. ID. NO: 4 induced coagulation of liposome more than the peptide represented by SEQ. ID. NO: 3 (see FIG. 5C).

The present inventors also investigated how the structure of the peptide of the invention could be changed in the course of the interaction with bacteria and erythrocyte-like liposome by using circular dichroism (CD). As a result, the peptides each represented by SEQ. ID. NO: 1 and SEQ. ID. NO: 2 did not form any specific structure in bacteria nor in erythrocyte-like liposome, while the peptides represented by SEQ. ID. NO: 3 and SEQ. ID. NO: 4 showed structural change with folding (see FIGS. 6A-6B). This phenomenon is regarded as an important factor to break bacterial membrane.

Further, the present inventors investigated the mechanism of antibacterial activity of the peptide of the invention in antibiotic-tolerant *E. coli* (*E. coli* CCARM 1229) by using scanning electron microscope. As a result, when *E. coli* was treated with the peptide represented by SEQ. ID. NO: 3, the smooth surface of the antibiotic-tolerant *E. coli* turned into rough and injured with showing aggregation as well (see FIGS. 7A-7B).

Therefore, the peptide of the present invention in which lysine and tryptophan residues are repeated 4 times demonstrates excellent antibacterial activity and fungicidal activity by affecting the inner membrane of the pathogenic microorganism but has least cytotoxicity, suggesting that the peptide of the invention can be effectively used as a safe antibacterial agent for human.

The present invention also provides an antibacterial or fungicidal pharmaceutical composition comprising the peptide of the invention as an active ingredient.

The present invention also provides a use of the said peptide for the preparation of an antibacterial or fungicidal pharmaceutical composition.

The present invention also provides the peptide usable for the suppression of pathogenic bacteria or fungi.

The present invention also provides a method for suppressing bacteria or fungi containing the step of treating a pharmaceutically effective dose of the said antibacterial or fungicidal pharmaceutical composition to the target bacteria or fungi to suppress them.

The said pharmaceutical composition has the antibacterial activity preferably against Gram-positive bacteria, Gram-negative bacteria, and antibiotic-tolerant strains, and more precisely the Gram-positive bacteria are selected from the group consisting of *Bacillus subtilis, Staphylococcus aureus* and *Listeria monocytogenes*, and the Gram-negative bacteria are selected from the group consisting of *Escherichia coli, Psedomonas aeruginosa* and *Salmonella typhimurium*. In the meantime, the antibiotic-tolerant strains are preferably selected from the group consisting of *E. coli* (*E. coli* CCARM 1229, 1238), *Salmonella* (*S. typhimurium* CCARM 8007, 8009, 8013) and *Staphylococcus* (*S. aureus* CCARM 3089, 3090, 3108, 3114, 3126), but not always limited thereto.

The said pharmaceutical composition has the fungicidal activity preferably against pathogenic fungi and antibiotic-tolerant fungi, and more precisely the said pathogenic fungi are selected from the group consisting of *Candida albicans, C. catenulate, C. intermidia, C. rugosa, C. glabrata* and *C. melibiosica*, and the antibiotic-tolerant fungi are preferably *C. albicans* CCARM 14001, 14007, and 14020, but not always limited thereto.

The peptide of the present invention in which lysine and tryptophan residues are repeated demonstrates excellent antibacterial activity and fungicidal activity by affecting the inner membrane of the pathogenic microorganism but has least cytotoxicity, suggesting that the peptide of the invention can be effectively used as an antibacterial and fungicidal pharmaceutical composition.

The novel peptide of the present invention can be administered orally or parenterally and be used in general forms of pharmaceutical formulation.

That is, the novel peptide of the present invention can be prepared for oral or parenteral administration by mixing with generally used diluents or excipients such as fillers, extenders, binders, wetting agents, disintegrating agents and surfactant. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The novel peptide of the present invention can be mixed with many pharmaceutically acceptable carriers such as physiological saline or organic solvent, and can additionally include carbohydrates such as glucose, sucrose or dextran, antioxidants such as ascorbic acid or glutathion, chelating agents, low molecular proteins or other stabilizers to enhance stability or absorptiveness.

The effective dose of the novel peptide of the present invention is 0.01~100 mg/kg, and more preferably 0.14~1.4 mg/kg, which can be administered 1~3 times a day.

The present invention also provides a method for treating the pathogenic bacteria or fungi caused disease containing the step of administering a pharmaceutically effective dose of the said antibacterial or fungicidal pharmaceutical composition to a subject having the pathogenic bacteria or fungi caused disease.

The present invention also provides a method for preventing the pathogenic bacteria or fungi caused disease containing the step of administering a pharmaceutically effective dose of the said antibacterial or fungicidal pharmaceutical composition to a subject.

The present invention also provides the peptide usable for treating or preventing the pathogenic bacteria or fungi caused disease.

The effective dose of the novel peptide of the present invention can be administered in the form of bolus, by single dose having relatively short period of infusion or by multiple dose of fractionated treatment protocol for a long term. The decision of the effective dose depends on the administration pathway, treatment times, age and other conditions of a patient, etc. Therefore, any expert who has knowledge on this field can decide the effective dose of the novel peptide of the present invention.

The present invention also provides an antibacterial or fungicidal cosmetic composition comprising the peptide of the invention as an active ingredient.

The present invention also provides a use of the said peptide for the preparation of an antibacterial or fungicidal cosmetic composition.

The peptide of the present invention in which lysine and tryptophan residues are repeated demonstrates excellent antibacterial activity and fungicidal activity by affecting the inner membrane of the pathogenic microorganism but has least cytotoxicity, suggesting that the peptide of the invention can be effectively used as an antibacterial and fungicidal cosmetic composition.

The cosmetic composition of the present invention can include, in addition to the said novel peptide, any conventional ingredients generally used in cosmetics, for example such additives and carriers as stabilizers, solubilizers, vitamins, pigments and flavors, but not always limited thereto.

The cosmetic composition of the present invention can be formulated in any form that can be accepted in the art, which is exemplified by solution, suspension, emulsion, paste, gel, cream, lotion, powder, soap, surfactant-containing cleansing, oil, powdered foundation, emulsified foundation, wax foundation and spray, but not always limited thereto. Particularly, the cosmetic composition of the present invention can be prepared in the form of soft lotion (skin), nutrition lotion (milk lotion), nutrition cream, massage cream, essence, eye cream, cleansing cream, cleansing foam, cleansing water, pack, spray or powder.

In the case that the cosmetic composition is formulated as paste, cream or gel, the proper carrier can be selected from the group consisting of animal oil, vegetable oil, paraffin, starch, tracanth, cellulose derivative, polyethylene glycol, silicon, bentonite, silica, talk and zinc oxide.

In the case that the cosmetic composition is formulated as powder or spray, the proper carrier can be selected from the group consisting of lactose, talc, silica, aluminum hydroxide, calcium silicate and polyamide powder, and in particular if the composition of the present invention is formulated as spray, a propellant such as chlorofluorohydrocarbon, propane/butane or dimethyl ether can be additionally included.

In the case that the cosmetic composition is formulated as liquid or emulsion, the proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the cosmetic composition is formulated as suspension, the proper carrier can be selected from the group consisting of liquid diluent such as water, ethanol or propylene glycol; suspending agent such as ethoxylated isostearyl alcohol, polyoxyethylene sorbitol ester and polyoxyethylene sorbitan ester; microcrystalline cellulose; aluminum methahydroxide; bentonite; agar; and tragacanth.

In the case that the cosmetic composition is formulated as surfactant-containing cleansing, the proper carrier can be selected from the group consisting of aliphatic alcohol sulfate, aliphatic alcohol ether sulfate, sulfosuccinic monoester, isethionate, imidazolinum derivative, methyltaurate, sarcosinate, fatty acid amide ether sulfate, alkyl amidobetain, aliphatic alcohol, fatty acid glyceride, fatty acid diethanolamide, vegetable oil, lanolin derivative and ethoxylated glycerol fatty acid ester.

The present invention also provides a non-toxic agricultural pesticide comprising the peptide of the invention as an active ingredient.

The present invention also provides a use of the said peptide for the preparation of a non-toxic agricultural pesticide.

The peptide of the present invention in which lysine and tryptophan residues are repeated demonstrates excellent antibacterial activity and fungicidal activity by affecting the inner membrane of the pathogenic microorganism but has least cytotoxicity, suggesting that the peptide of the invention can be effectively used as a non-toxic agricultural pesticide.

The present invention also provides a preservative for medicine, cosmetics, food, or feed comprising the peptide of the invention as an active ingredient.

The present invention also provides a use of the said peptide for the preparation of a preservative for medicine, cosmetics, food, or feed.

The peptide of the present invention in which lysine and tryptophan residues are repeated demonstrates excellent antibacterial activity and fungicidal activity by affecting the inner membrane of the pathogenic microorganism but has least cytotoxicity, suggesting that the peptide of the invention can be effectively used as a preservative for medicine, cosmetics, food, or feed.

The preservative for food, cosmetics, or medicine is the additive used to prevent spoilage, decomposition, and chemical changes, which includes germicides and antioxidants, etc. Functional antibiotics suppressing the growth of microorganisms including bacteria, fungi, and yeasts can be also included to prevent the growth of spoilage microorganisms in medicine and food. Such preservative for food, cosmetics, or medicine is expected to be non-toxic and is effective even at a low concentration. Agricultural pesticides to prevent damages by blight and insects in agricultural crops are also expected to inhibit the growth of harmful microorganisms but expected to be non-toxic to human in order for human to eat the agricultural product safely.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Peptide Synthesis, Separation and Purification

To synthesize the peptide having the repeats of lysine and tryptophan, the present inventors used Merrifield's liquid-solid method (Merrifield, R B., *J. Am. Chem. Soc.*, 85, 2149, 1963) using Fmoc (9-fluorenylmethoxy carbonyl) as the amino acid protecting group. Particularly, Rink Amide MBHA-Resin was used as a starting material for the peptide having —$NH_2$ type C-terminal, and Fmoc-amino acid-Wang Resin (Wang Resin) was used as a starting material for the peptide having —OH type C-terminal. The peptide chain extension via Fmoc-amino acid coupling was performed by DCC (N-hydroxybenzo triazole(HOBt)-dicyclo-hexycarbodiimide) method. After Fmoc-amino acids at N-terminal of each peptide were coupled, Fmoc group was eliminated by using NMP (20% piperidine/N-methyl pyrolidone) solution, followed by washing with NMP and DCM (dichoromethane) several times and drying over nitrogen gas. TFA (trifluoroacetic acid)-phenol-thioanisole-$H_2O$-triisopropylsilane (85:5:5:2.5:2.5, vol./vol.) solution was added thereto, followed by reaction for 2~3 hours to eliminate the protecting group and separate the peptide from the regin. The peptide was precipitated by using diethylether. The crude peptide obtained thereby was purified by reverse phase (RP)-HPLC column (Delta Pak, $C_{18}$ 300 Å, 15, 19.0 mm×30 cm, Waters) in acetonitrile gradient containing 0.05% TFA. The synthesized peptide was hydrolyzed with 6N HCl at 110° C., and the residue was concentrated under reduced pressure. After dissolving the concentrate in 0.02 N HCl, amino acid composition was analyzed with an amino acid analyzer (Hitachi 8500 A).

Figure 1:
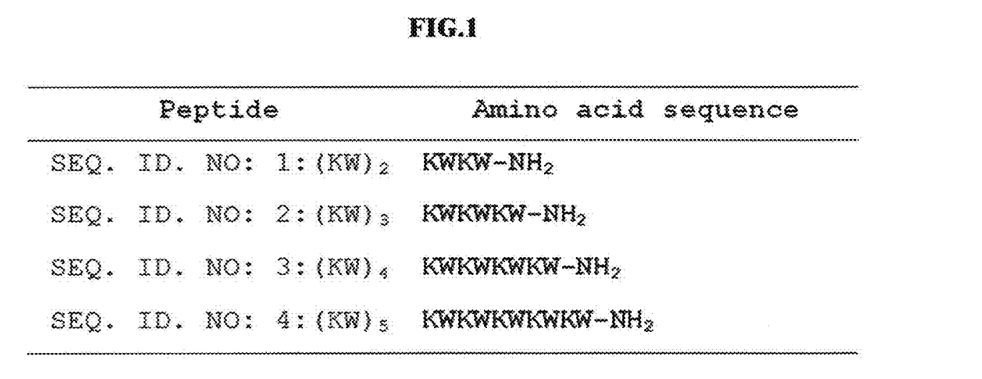
FIG. 1 is a diagram illustrating the peptide of the present invention and the sequence thereof.

As a result, as shown in FIG. 1, the peptide having the wanted amino acid sequence was successfully synthesized (FIG. 1).

Example 2: Measurement of Antibacterial Activity of Peptide

<2-1> Measurement of MIC in Bacteria

To measure the antibacterial activity of the peptide prepared in Example 1, the present inventors measured MIC, the minimal concentration that can keep the strain without being divided. For the measurement of antibacterial activity, Gram-positive bacteria selected from the group consisting of *Bacillus subtilis*, *Staphylococcus aureus* and *Listeria monocytogenes*, Gram-negative bacteria selected from the group consisting of *Escherichia coli*, *Psedomonas aeruginosa* and *Salmonella typhimurium*, and antibiotic-tolerant strains selected from the group consisting of *E. coli* (*E. coli* CCARM 1229, 1238), *Salmonella* (*S. typhimurium* CCARM 8007, 8009, 8013) and *Staphylococcus* (*S. aureus* CCARM 3089, 3090, 3108, 3114, 3126) were used. After cultured in optimal media, the strains were diluted at the density of 2×10⁵ cells/ml, which were then inoculated on microtitrate plates. The peptide synthesized in Example 1 and the positive control peptide (Melittin) were 2-fold diluted in sodium phosphate buffer and phosphate buffered saline (PBS) from 200 μM/well, which were added in the plate, followed by culture at 37° C. for 18~24 hours. $OD_{620}$ was measured with a microtitrate plate reader to determine MIC of each strain. The results are presented in Table 1 (the number in bracket indicates the one obtained from PBS).

As a result, as shown in Table 1, the peptide represented by SEQ. ID. NO: 3 of the present invention displayed 64 times higher antibacterial activity in general strains than the peptide represented by SEQ. ID. NO: 1, 16 times higher antibacterial activity than the peptide represented by SEQ. ID. NO: 2, and 8 times higher antibacterial activity than the peptide represented by SEQ. ID. NO: 4. In the meantime, in antibiotic-tolerant strains, the peptide of the present invention demonstrated 32 times higher antibacterial activity than the peptide represented by SEQ. ID. NO: 1, 8 times higher antibacterial activity than the peptide represented by SEQ. ID. NO: 2, and 8 times higher antibacterial activity than the peptide represented by SEQ. ID. NO: (Table 1).

TABLE 1

MIC of peptide in bacteria
MIC (μM)

| Microorganism | SEQ. ID. NO: 1 | SEQ. ID. NO: 2 | SEQ. ID. NO: 3 | SEQ. ID. NO: 4 | Melittin | Ampicillin | Oxacillin |
|---|---|---|---|---|---|---|---|
| Gram negative bacteria | | | | | | | |
| *E. coil* | >200 (>200) | 50 (200) | 6.25 (12.5) | 50 (12.5) | 1.56 (1.56) | — | — |
| *S. typhimurium* | 50 (200) | 3.12 (6.25) | 1.56 (1.56) | 6.25 (3.12) | 0.39 (0.39) | — | — |

TABLE 1-continued

| | MIC of peptide in bacteria MIC (μM) | | | | | | |
|---|---|---|---|---|---|---|---|
| Microorganism | SEQ. ID. NO: 1 | SEQ. ID. NO: 2 | SEQ. ID. NO: 3 | SEQ. ID. NO: 4 | Melittin | Ampicillin | Oxacillin |
| *P. aeruginosa* | >200 (>200) | 12.5 (25) | 3.12 (3.12) | 25 (6.25) | 3.12 (3.12) | — | — |
| Gram positive bacteria | | | | | | | |
| *S. aureus* | >200 (>200) | 50 (200) | 6.25 (12.5) | 25 (12.5) | 1.56 (1.56) | — | — |
| *B. subtilis* | >200 (>200) | 100 (200) | 6.25 (12.5) | 12.5 (12.5) | 1.56 (3.12) | — | — |
| *L. monocytogenes* | 200 (>200) | 12.5 (25) | 3.12 (3.12) | 3.12 (3.12) | 1.56 (1.56) | — | — |
| antibiotic-tolerant strains | | | | | | | |
| *E. coli* CCARM 1229[a] | >200 (>200) | 25 (100) | 6.25 (12.5) | 50 (12.5) | 3.12 (3.12) | >200 (>200) | |
| *E. coli* CCARM 1238[a] | >200 (>200) | 50 (200) | 12.5 (12.5) | 50 (12.5) | 1.56 (1.56) | >200 (>200) | |
| *S. typhimurium* CCARM 8007[b] | >200 (>200) | 50 (200) | 12.5 (12.5) | 25 (12.5) | 6.25 (12.5) | >200 (>200) | |
| *S. typhimurium* CCARM 8009[b] | >200 (>200) | 50 (200) | 6.25 (12.5) | 25 (12.5) | 6.25 (12.5) | >200 (>200) | |
| *S. typhimurium* CCARM 8013[b] | >200 (>200) | 50 (200) | 6.25 (12.5) | 25 (12.5) | 3.12 (6.25) | >200 (>200) | |
| *S. aureus* CCARM 3089[c] | >200 (>200) | 50 (200) | 12.5 (12.5) | 50 (12.5) | 1.56 (1.56) | — | >200 (>200) |
| *S. aureus* CCARM 3090[c] | >200 (>200) | 50 (200) | 12.5 (12.5) | 25 (12.5) | 3.12 (3.12) | — | >200 (>200) |
| *S. aureus* CCARM 3108[c] | >200 (>200) | 50 (200) | 12.5 (12.5) | 50 (12.5) | 1.56 (1.56) | — | >200 (>200) |
| *S. aureus* CCARM 3114[c] | >200 (>200) | 50 (200) | 12.5 (12.5) | 25 (12.5) | 3.12 (3.12) | — | >200 (>200) |
| *S. aureus* CCARM 3126[c] | >200 (>200) | 50 (200) | 12.5 (12.5) | 25 (12.5) | 1.56 (1.56) | — | >200 (>200) |

<2-2> Measurement of MIC in Fungi

To measure the fungicidal activity of the peptide prepared in Example 1, the present inventors measured MIC, the minimal concentration that can keep the strain without being divided. For the measurement of fungicidal activity, pathogenic fungi selected from the group consisting of *Candida albicans, C. catenulate, C. intermidia, C. rugosa, C. glabrata* and *C. melibiosica* were used. After cultured in optimal media, the strains were diluted at the density of $2 \times 10^5$ cells/ml, which were then inoculated on microtitrate plates. The peptide synthesized in Example 1 and the positive control peptide (Melittin) were 2-fold diluted in solution 1 (10 mM sodium phosphate buffer, pH 7.2) and solution 2 (phosphate buffered saline) from 128 μM/well, which were added in the plate, followed by culture at 37° C. for 18~24 hours. $OD_{620}$ was measured with a microtitrate plate reader to determine MIC of each strain. The results are presented in Table 2.

As a result, as shown in Table 2, the peptide of the present invention represented by SEQ. ID. NO: 3 demonstrated excellent fungicidal activity in any solution, while the peptide represented by SEQ. ID. NO: 4 showed better fungicidal activity in solution 2 (phosphate buffered saline) (Table 2).

TABLE 2

| | MIC of peptide in fungi MIC (μm) | | | | | | | | | |
|---|---|---|---|---|---|---|---|---|---|---|
| | SEQ. ID. NO: 1 | | SEQ. ID. NO: 2 | | SEQ. ID. NO: 3 | | SEQ. ID. NO: 4 | | Melittin | |
| Microorganism | Sol. 1 | Sol. 2 | Sol. 1 | Sol. 2 | Sol. 1 | Sol. 2 | Sol. 1 | Sol. 2 | Sol. 1 | Sol. 2 |
| *C. albicans* | >128 | >128 | 8 | 32 | 8 | 8 | 16 | 8 | 4 | 4 |
| *C. catenulate* | >128 | >128 | 8 | 16 | 8 | 8 | 32 | 8 | 4 | 8 |
| *C. intermidia* | >128 | >128 | 8 | 32 | 8 | 8 | 32 | 4 | 4 | 4 |
| *C. rugosa* | >128 | >128 | 8 | 32 | 8 | 8 | 32 | 8 | 4 | 8 |
| *C. glabrata* | >128 | >128 | 16 | 32 | 8 | 8 | 16 | 4 | 4 | 4 |
| *C. melibiosica* | >128 | >128 | 8 | 32 | 8 | 8 | 32 | 8 | 4 | 8 |

To measure the fungicidal activity of the peptide of the present invention in antibiotic-tolerant fungi, MIC of the peptide was measured by the same manner as described in Example <2-2> using RMPI 1640 and antibiotic-tolerant *Candida albicans* (*C. albicans* CCARM 14001, 14007, 14020). The results are presented in Table 3.

As a result, as shown in Table 3, the peptides represented by SEQ. ID. NO: 3 and SEQ. ID. NO: 4 demonstrated excellent fungicidal activity (Table 3).

TABLE 3

MIC of peptide in antibiotic-tolerant fungi

| Microorganism | MIC (μm) | | | | | |
|---|---|---|---|---|---|---|
| | SEQ. ID. NO: 1 | SEQ. ID. NO: 2 | SEQ. ID. NO: 3 | SEQ. ID. NO: 4 | Melittin | Fluconazole |
| *C. albicans* CCARM 14001 | >128 | >128 | 32 | 8 | 16 | >128 |
| *C. albicans* CCARM 14007 | >128 | >128 | 32 | 16 | 8 | >128 |
| *C. albicans* CCARM 14020 | >128 | >128 | 32 | 8 | 8 | >128 |

Example 3: Measurement of Cytotoxicity of Peptide

To investigate whether or not the peptide of the present invention had cytotoxicity, the present inventors investigated hemolytic activity of the peptide. Particularly, human erythrocytes were diluted in phosphate buffered saline (PBS, pH 7.0) at the concentration of 8%, to which the peptide 2-fold diluted from 200 μM/well was added, followed by reaction at 37° C. for 1 hour. Centrifugation was performed at 1,000 g and the level of hemoglobin included in the supernatant was measured by measuring $OD_{414}$. To examine hemolysis, 1% triton X-100 was added to human erythrocytes, followed by measuring absorbance of the supernatant. The hemolytic activity of 1% triton X-100 was regarded as 100%, with which hemolytic activity of each antibacterial peptide was compared. The result was presented by the numbers calculated by the following mathematical formula 1.

% hemolysis=(absorbance *A*−absorbance *B*/absorbance *A*−absorbance *B*)×100   [Mathematical Formula 1]

In the above formula, absorbance A indicates the absorbance of the peptide solution measured at 414 nm, absorbance B indicates the absorbance of PBS measured at 414 nm, and absorbance C indicates the absorbance of 1% triton X-100 measured at 414 nm.

The hemolytic activity at the concentration of 200 μM, calculated by the formula, is presented in Table 4.

As shown in Table 4, the peptides of the present invention represented respectively by SEQ. ID. NO: 1, SEQ. ID. NO: 2, and SEQ. ID. NO: 3 hardly showed cytotoxicity, while the peptide of the positive control represented by SEQ. ID. NO: 4 clearly displayed significant cytotoxicity (Table 4).

TABLE 4

| | Hemolysis (%) | | | | | | |
|---|---|---|---|---|---|---|---|
| | SEQ. ID. NO: 1 | SEQ. ID. NO: 2 | SEQ. ID. NO: 3 | SEQ. ID. NO: 4 | Melittin | Ampicillin | Oxacillin |
| Hemolytic activity | 0 | 0 | 8 | 71 | 100 | — | — |

Example 4: Analysis of Peptide Aggregation and Structure

<4-1> Investigation of Peptide Aggregation by Spectrofluorometer

To investigate whether or not the peptide of the present invention show aggregation in aqueous solution, the present inventors dissolved the peptide in two aqueous solutions at different concentrations, followed by investigation of peptide aggregation. Tryptophan, one of the amino acids composing peptide, has the characteristics of emitting fluorescence, by using which aggregation of the peptide can be confirmed. The peptide was dissolved in water and in PBS at different concentrations (1~18 μM). Changes of fluorescence emission rate were recorded by using a spectrofluorometer (Perkin-Elmer LS55). Excitation wavelength used for the measurement was 280 nm and emission wavelength was 300~400 nm.

Figure 2A:
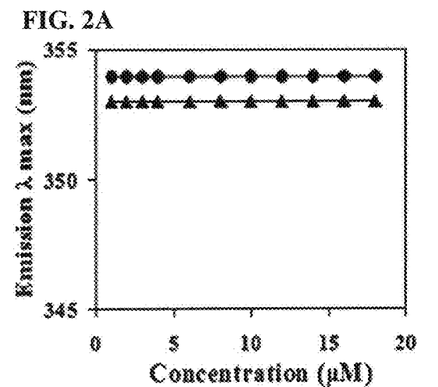
FIGS. 2A and 2B are graphs illustrating the maximum fluorescent light emission wavelength of tryptophan residue in the peptide of the invention measured in order to analyze aggregation over the concentration of the peptide in water and PBS.
Figure 2B:
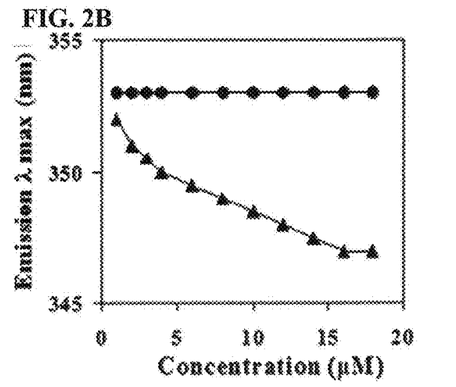

As a result, as shown in FIG. 2A, the maximum fluorescent light emission wavelength values of those peptides of the present invention represented by SEQ. ID. NO: 3 and NO: 4 did not change over the concentrations (FIG. 2A). On the contrary, as shown in FIG. 2B, the maximum fluorescent light emission wavelength of the peptide represented by SEQ. ID. NO: was reduced as the concentration of the peptide increased in PBS, while the maximum fluorescent light emission wavelength of the peptide represented by SEQ. ID. NO: 3 did not change in PBS (FIG. 2B). Therefore, it was confirmed that the peptide represented by SEQ. ID. NO: 3 did not show aggregation in both aqueous solutions but the peptide represented by SEQ. ID. NO: 4 was aggregated in PBS.

<4-2> Investigation of Aggregation by Circular Dichroism (CD)

Peptide aggregation over different concentrations in PBS was measured by circular dichroism (CD). Particularly, different concentrations of the peptide were loaded in CD cuvette, followed by analysis at 190~250 nm.

Figure 2C:
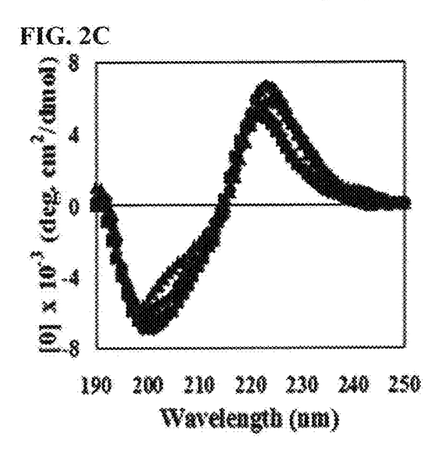
FIGS. 2C and 2D are graphs illustrating the secondary structure of the peptide in PBS analyzed by circular dichroism (CD).
Figure 2D:
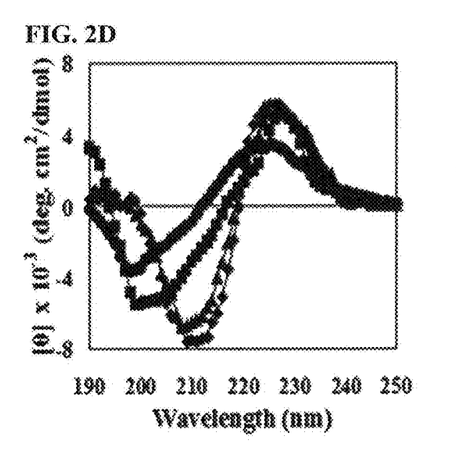

As a result, as shown in FIGS. 2C and 2D, the peptide of the present invention represented by SEQ. ID. NO: 3 made the consistent graph in PBS regardless of concentrations. In the meantime, the graph representing the peptide represented by SEQ. ID. NO: 4 showed up and down (FIGS. 2C and 2D). Therefore, as indicated in the result shown in FIG. 2B, the peptide represented by SEQ. ID. NO: 3 was not aggregated in PBS, but the peptide represented by SEQ. ID. NO: 4 was aggregated therein.

Example 5: Confirmation of Active Site of the Peptide in Bacteria

To confirm the active site of the peptide of the present invention in *E. coli*, the present inventors used confocal laser scanning microscopy. The antibiotic-tolerant *E. coli* (*E. coli* CCARM 1229) and the antibiotic-tolerant *Staphylococcus* aureus (*S. aureus* CCARM 3090) were cultured in each optimal medium for them, followed by dilution in PBS at the density of 2×10$^5$ cells/a. 12.5 µM of the peptide represented by SEQ. ID. NO: 3 labeled with 5-carboxytetramethylrhodamine (TAMRA) was treated to the *E. coli* and *Staphylococcus aureus*, followed by reaction at 37° C. for 10 minutes. Centrifugation was performed at 3000 g for 5 minutes and those two bacteria were recovered and washed with PBS, which process was repeated three times. The treated two bacteria were observed under confocal laser scanning microscope.

Figure 3A:
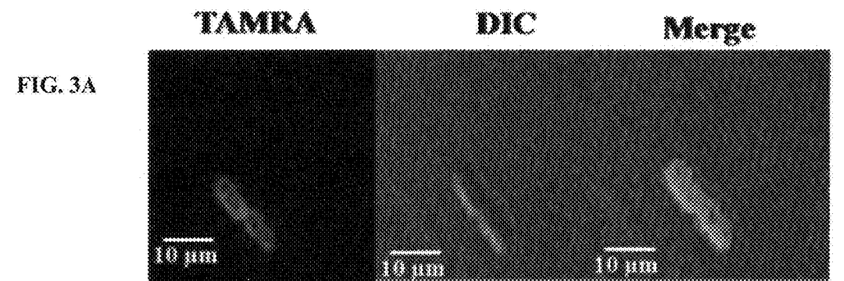
FIGS. 3A-3B are a diagram illustrating the acting location of the peptide of the present invention, for which the peptide was labeled with a fluorescent material and then treated to bacteria.
Figure 3B:
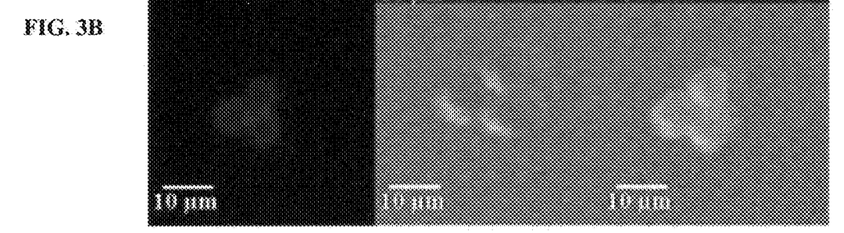

As a result, as shown in FIGS. 3A and 3B, the peptide of the present invention represented by SEQ. ID. NO: 3 was confirmed to be conjugated onto the outer wall of the antibiotic-tolerant *E. coli* and the antibiotic-tolerant *Staphylococcus aureus* (FIGS. 3A and 3B).

Example 6: Investigation of Effect of the Peptide on *E. coli* Membrane

<6-1> Analysis of Depolarization of Bacteria

To investigate depolarization of bacteria, the antibiotic-tolerant *E. coli* (*E. coli* CCARM 1229) and the antibiotic-tolerant *Staphylococcus aureus* (*S. aureus* CCARM 3090) were cultured in each optimal medium for them, and then washed with buffer 1 (20 mM glucose, 5 mM HEPES, pH 7.3) twice. The culture media was diluted with buffer 2 (20 mM glucose, 5 mM HEPES, 0.1 M KCl, pH 7.3) until OD$_{600}$ of each bacterium reached 0.05. 1 µM of 3,3'-diethylthiodicarbocyanine iodide (DiSC3-5) was added thereto, followed by reaction until the standard fluorescence was stable. Then, the peptide was treated thereto at different concentrations and the changes of fluorescence emission rate were recorded. Excitation wavelength used for the measurement was 622 nm and emission wavelength was 670 nm.

Figure 4A:
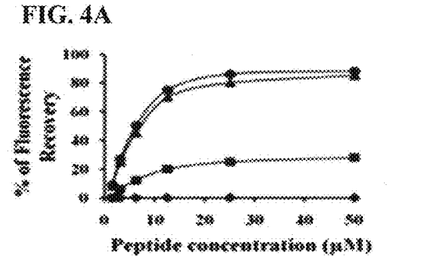
FIGS. 4A-4F show graphs illustrating the effect of the peptide of the present invention on bacterial membrane and the duration of bactericidal action according to the concentration of the peptide.
Figure 4B:
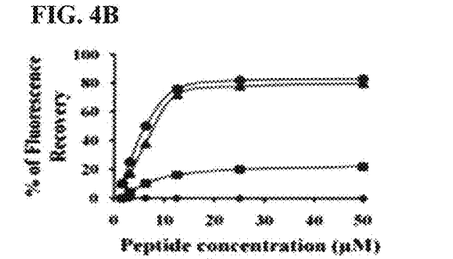

As a result, as shown in FIGS. 4A and 4B, the peptide represented by SEQ. ID. NO: 1 could not induce depolarization of membrane in both bacteria, while the peptide represented by SEQ. ID. NO: 2 induced depolarization approximately 20% at the concentration of 50 µM. In the meantime, the peptides represented by SEQ. ID. NO: 3 and SEQ. ID. NO: 4 all induced depolarization approximately 80% at the concentration of 25 µM (FIGS. 4A and 4B).

<6-2> Confirmation of Effect on Inner Membrane

To investigate whether or not the peptide of the present invention affected the inner membrane, *E. coli* and *S. aureus* were cultured in each optimal medium for them, and then diluted in PBS at the density of 2×10$^7$ cells/ml. The cells were reacted with 1 µM SYTOX green (molecular probe) in the darkness for 10 minutes, to which 12.5 µM of the peptide above was treated. Thereafter, fluorescence was measured for one hour. Excitation wavelength used for the measurement was 485 nm and emission wavelength was 520 nm. The value obtained after treating 0.1% triton X-100 was regarded as 100%, by which the comparative fluorescence emission rate was measured.

Figure 4C:
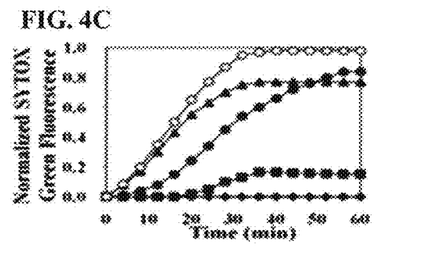
Figure 4D:
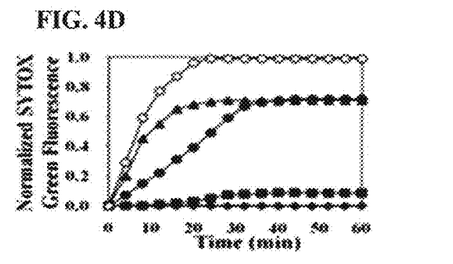

As a result, as shown in FIGS. 4C and 4D, the peptide represented by SEQ. ID. NO: 4 demonstrated the highest fluorescence emission rate at the time point of 30 min. in *E. coli* and at the time point of min. in *Staphylococcus aureus*, while the peptide represented by SEQ. ID. NO: 3 demonstrated the highest fluorescence emission rate at the time point of 56 min. in *E. coli* and at the time point of 30 min. in *Staphylococcus aureus*. The above results indicate that the peptides represented respectively by SEQ. ID. NO: 3 and SEQ. ID. NO: 4 could affect the inner membrane of *E. coli* and *Staphylococcus aureus* (FIGS. 4C and 4D)

<6-3> Confirmation of Time Dependent Apoptosis

To investigate time dependent apoptosis, the antibiotic-tolerant *E. coli* (*E. coli* CCARM 1229) and the antibiotic-tolerant *Staphylococcus aureus* (*S. aureus* CCARM 3090) were cultured in optimal media respectively. The bacteria (2×10$^5$ cells/a) were treated with the peptide at the concentration of MIC and double the MIC, followed by reaction for 0, 1, 3, 5, 10, 20, 30, 40, 50, and 60 minutes. A portion thereof was diluted and smeared on agar media. After culturing the media for 16 hours at 37° C., the number of colonies generated thereon was counted.

Figure 4E:
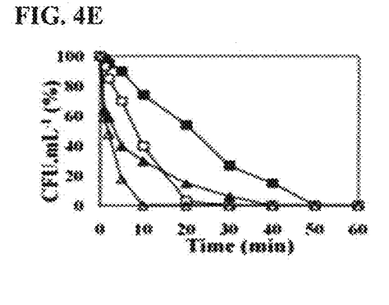
Figure 4F:
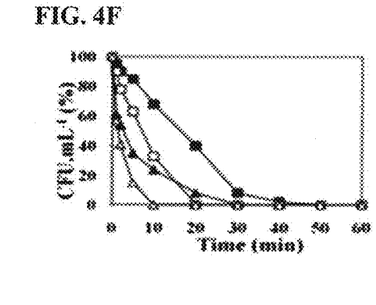

As a result, as shown in FIGS. 4E and 4F, the peptide represented by SEQ. ID. NO: 3 demonstrated bactericidal activity after 20 minutes of culture at the concentration of MIC and after 10 minutes of culture at the concentration of double the MIC in both bacteria. In the meantime, the peptide represented by SEQ. ID. NO: 4 showed bactericidal activity after 50 minutes of culture at the concentration of MIC and after 35 minutes of culture at the concentration of double the MIC. The above results indicate that the peptide represented by SEQ. ID. NO: 3 works to kill both antibiotic-tolerant bacteria faster than the peptide represented by SEQ. ID. NO: 4 does (FIGS. 4E and 4F).

Example 7: Interaction Between the Peptide and Bacteria/Erythrocyte-Like Liposome <7-1> Investigation of Interaction Between the Peptide and Bacteria/Erythrocyte-Like Liposome To investigate whether or not the peptide of the present invention interacted with bacteria and erythrocyte-like liposome, the present inventors first prepared bacteria and erythrocyte-like liposome. *E. coli* membrane is mostly composed of L-a-phosphatidylethanolamine (PE) and L-a-phosphatidylglycerol (PG) and erythrocyte (human red blood cell) membrane is composed of egg yolk L-a-phosphatidylcholine (PC) and cholesterol (CH). PE and PG were dissolved at the ratio of 7:3 in chloroform solution. PC and CH were dissolved at the ratio of 10:1 in the same solution. The prepared solutions were loaded in glass tubes and moisture was eliminated, followed by freeze-drying. PBS (phosphate buffered saline, pH 7.4) containing calcein (70 mM) fluorescence sample was loaded in the glass tube, which was frozen with liquid nitrogen and then thawed. This freezing and thawing process was repeated 9 times. To isolate the fluorescence sample that did not flow in liposome, gel filtration chromatography was performed. The liposome harboring fluorescence sample containing 2.5 µM of lipid was reacted with the peptide at different concentrations (0.03~1 µM) for 25 minutes. Fluorescence emitted from the fluorescence sample was measured with a spectrofluorometer. Excitation wavelength used for the measurement was 480 nm and emission wavelength was 520 nm. Emission rate measured in the presence of 0.1% triton X-100 was regarded as 100%, which became the standard. Based on this standard value, emission rate of each peptide was calculated according to the below mathematical formula 2 and then compared.

% fluorescence emission rate=
$(F-F_0)/(F_t-F_0)\times 100$  [Mathematical Formula 2]

In the formula, F indicates the absorbance after treated with the peptide, $F_0$ indicates the absorbance after treated with buffer, and $F_t$ indicates the absorbance after treated with 0.1% triton X-100. Fluorescence emission rate was investigated at different concentrations of the peptide.

Figure 5A:
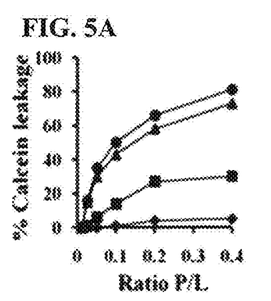
FIGS. 5A-5C are graphs illustrating the emission of the fluorescent material and the cohesiveness measured in order to confirm whether or not the peptide of the present invention could work on the bacteria-like double membrane.
Figure 5B:
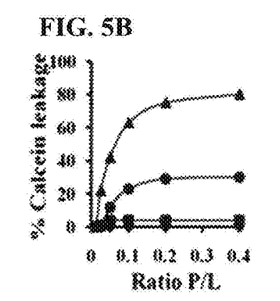

As a result, as shown in FIG. 5A, the peptides represented by SEQ. ID. NO: 3 and SEQ. ID. NO: 4 emitted fluorescence a lot, indicating that these peptides interacted with bacteria-like liposome. When compared between these two peptides, as shown in FIG. 5B, the peptide represented by SEQ. ID. NO: 3 emitted fluorescence at most half the level emitted by the peptide represented by SEQ. ID. NO: 4 at the same concentration (FIGS. 5A and 5B).

<7-2> Investigation of Erythrocyte-Like Liposome Aggregation by the Peptide

To investigate whether or not the peptide of the present invention could induce aggregation of erythrocyte-like liposome, PE and PG were dissolved in chloroform at the ratio of 7:3, which was loaded in a glass tube. Moisture was eliminated therefrom, followed by freeze-drying. PBS was loaded in the glass tube, which was frozen with liquid nitrogen and then thawed. This freezing and thawing process was repeated 9 times. Then, the solution passed through 0.2 μm filter membrane, and the filtrate was collected. The peptide was added to 400 μM liposome at the concentrations of 5, 10, 20, and 40 μM. $OD_{405}$ was measured to examine aggregation.

Figure 5C:
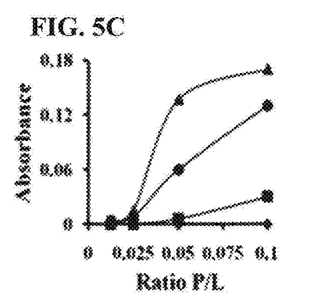

As a result, as shown in FIG. 5C, the peptide represented by SEQ. ID. NO: 4 induced aggregation of liposome more than the peptide represented by SEQ. ID. NO: 3 did (FIG. 5C).

Example 8: Analysis of Peptide Structure in Bacteria/Erythrocyte-Like Liposome

To investigate how the structure of the peptide of the present invention could be changed in bacteria and erythrocyte-like liposome, the present inventors first prepared bacteria and erythrocyte-like liposome by the same manner as described in Example <7-1>. The peptide structure in those liposome having artificial membrane was analyzed by circular dichroism (CD). 1 mM liposome and 50 μM were mixed, which was loaded in CD cuvette. Absorbance was measured at 190-250 nm.

Figure 6A:
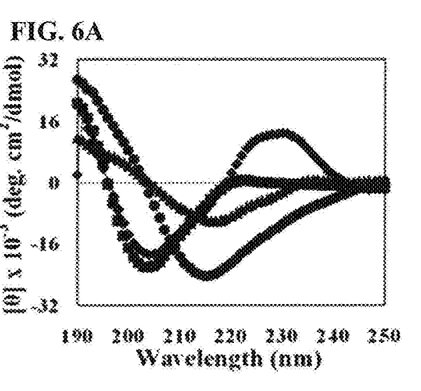
FIGS. 6A and 6B are graphs illustrating the secondary structure of the peptide of the present invention in the presence of the bacteria-like double membrane analyzed by circular dichroism (CD).
Figure 6B:
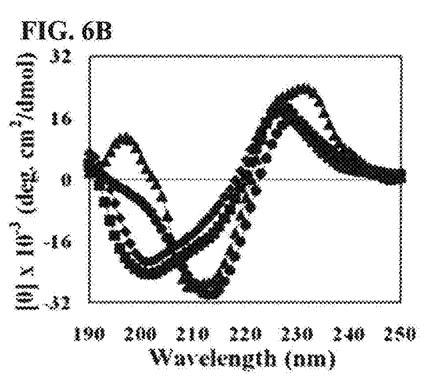

As a result, as shown in FIGS. 6A and 6B, the peptides represented by SEQ. ID. NO: 1 and SEQ. ID. NO: 2 did not form any specific structure in the bacteria-like liposome composed of PE and PG at the ratio of 7:3 nor in the erythrocyte-like liposome composed of PC and CH at the ratio of 10:1. On the contrary, the peptides represented by SEQ. ID. NO: 3 and SEQ. ID. NO: 4 showed a structural change of folding in both conditions (FIGS. 6A and 6B).

Example 9: Effect of the Peptide on Antibiotic-Tolerant E. coli

To investigate the activity of the peptide of the present invention on the antibiotic-tolerant E. coli (E. coli CCARM 1229), the present inventors used scanning electron microscope. The antibiotic-tolerant E. coli was cultured in optimal medium and the cells were diluted in PBS at the density of $2 \times 10^7$ cells/ml. The peptide represented by SEQ. ID. NO: 3 was added thereto at the concentration of 12.5 μM. minutes later, centrifugation was performed at 3000 g for 5 minutes. The precipitate was washed with PBS and then precipitated again, which was repeated twice. The bacteria were fixed with 500 μl of 5% glutaraldehyde in 0.2 M sodium-cacodylate buffer (pH 7.4) at 4° C. for 3hours and then washed with 0.1 M sodium-cacodylate buffer. Then, the bacteria were treated with 1% osmium tetroxide in 0.1 M sodium-cacodylate buffer, followed by reaction at 4° C. for 1 hour. The bacteria were then washed with the same buffer containing 5% sucrose twice. Dehydration was performed with 20, 40, 60, 80, 95, and 100% ethanol. After drying and coating, the bacteria were observed under scanning electron microscope.

Figure 7A:
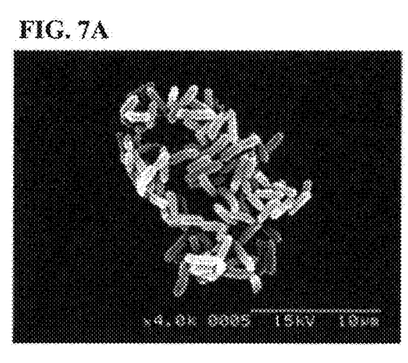
FIGS. 7A and 7B are electron micrographs illustrating the activity of the peptide of the present invention on antibiotic-tolerant *E. coli* (*E. coli* CCARM 1229) treated with the peptide.
Figure 7B:
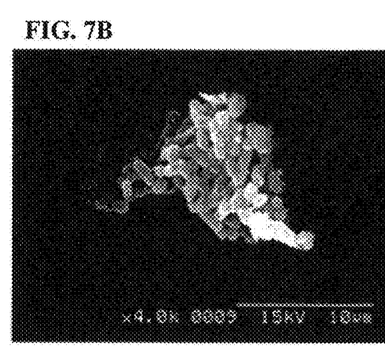

As a result, as shown in FIG. 7a, the surface of E. coli that was not treated with the peptide was smooth, but as shown in FIG. 7B, the surface of E. coli treated with the peptide represented by SEQ. ID. NO: 3 was rough and injured, indicating aggregation as well (FIGS. 7A and 7B).

The Manufacturing Examples of the composition for the present invention are described hereinafter.

Manufacturing Example 1: Preparation of Pharmaceutical Formulations

<1-1> Preparation of Powders

| | |
|---|---|
| Peptide of Example 1 | 2 g |
| Lactose | 1 g |

Powders were prepared by mixing all the above components, which were filled in airtight packs according to the conventional method for preparing powders.

<1-2> Preparation of Tablets

| | |
|---|---|
| Peptide of Example 1 | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Peptide of Example 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Peptide of Example 1 | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Peptide of Example 1 | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for inhibiting bacterial or fungal activity, comprising the step of exposing bacteria or fungi to a pharmaceutically effective dose of the peptide KWKWK-WKW-NH2 (SEQ ID NO: 3) in an amount that is safe for humans and sufficient to inhibit the bacterial or fungal activity, wherein the peptide has an —NH2 at the C-terminus.

2. The method according to claim 1, wherein the peptide is exposed to a pathogenic bacteria, and the pharmaceutically effective dose is sufficient to inhibit growth of the bacteria.

3. The method of claim 2, wherein the peptide is exposed to Gram positive bacteria.

4. The method according to claim 3, wherein the Gram-positive bacteria to which the peptide is exposed is *Bacillus subtilis, Staphylococcus aureus* or *Listeria monocytogenes.*

5. The method according to claim 2, wherein the peptide is exposed to Gram-negative bacteria.

6. The method according to claim 5, wherein the Gram-negative bacteria to which the peptide is exposed is *Escherichia coli, Pseudomonas aeruginosa* or *Salmonella typhimurium.*

7. The method according to claim 2, wherein the peptide is exposed to antibiotic-resistant strains of bacteria.

8. The method according to claim 7, wherein the antibiotic-resistant strain to which the peptide is exposed is antibiotic-resistant *E. coli*, antibiotic-resistant *Salmonella*, or antibiotic-resistant *Staphylococcus*.

9. The method according to claim 1, wherein the peptide is exposed to pathogenic fungi.

10. The method according to claim 9, wherein the pathogenic fungi to which the peptide is exposed is *Candida albicans, Candida catenulate, Candida intermedia, Candida rugosa, Candida glabrata* or *Candida melibiosica*.

11. The method according to claim 1, wherein the peptide is exposed to antibiotic-resistant fungi.

12. The method according to claim 11, wherein the antibiotic-resistant fungi to which the peptide is exposed is antibiotic-resistant *Candida albicans*.

13. The method of claim 1, wherein the peptide is exposed to the bacteria or fungi by administering the peptide to a subject having a bacterial or fungal infection, or by including the peptide in a composition to inhibit bacterial of fungal growth in the composition.

14. The method of claim 13, wherein the composition is a pharmaceutical composition, cosmetic, food or feed.

15. The method of claim 13, wherein the peptide is administered to the subject in a pharmaceutical composition.

16. The method of claim 15, wherein the pharmaceutical composition is administered orally or parenterally to the subject.

17. A method for treating disease caused by pathogenic bacteria or fungi, comprising the step of administering a pharmaceutically effective dose of an antibacterial or fungicidal peptide consisting of KWKWKWKW-NH2 (SEQ ID NO: 3), with an NH2 at the C-terminus, to a subject having the disease caused by the pathogenic bacteria or fungi, wherein the pharmaceutically effective dose is sufficient to inhibit growth of the pathogenic bacteria or fungi.

18. The method of claim 1, wherein the dose is 0.01-100 mg/kg.

* * * * *